(12) United States Patent
Jasper et al.

(10) Patent No.: US 9,777,217 B2
(45) Date of Patent: Oct. 3, 2017

US009777217B2

(54) COMPOUNDS HAVING A C—C TRIPLE BOND

(75) Inventors: Christian Jasper, Seligenstadt (DE); Constanze Brocke, Gross-Gerau (DE); Detlef Pauluth, Ober-Ramstadt (DE); Volker Reiffenrath, Rossdorf (DE); Atsutaka Manabe, Bensheim (DE)

(73) Assignee: MERCK PATENT GMBH, Darmstadt (DE)

( * ) Notice: Subject to any disclaimer, the term of this patent is extended or adjusted under 35 U.S.C. 154(b) by 56 days.

(21) Appl. No.: 14/005,839

(22) PCT Filed: Feb. 27, 2012

(86) PCT No.: PCT/EP2012/000828
§ 371 (c)(1),
(2), (4) Date: Sep. 18, 2013

(87) PCT Pub. No.: WO2012/126564
PCT Pub. Date: Sep. 27, 2012

(65) Prior Publication Data
US 2014/0008573 A1 Jan. 9, 2014

(30) Foreign Application Priority Data
Mar. 24, 2011 (DE) .......... 10 2011 015 043

(51) Int. Cl.
| | | |
|---|---|---|
| *C09K 19/30* | (2006.01) | |
| *C09K 19/32* | (2006.01) | |
| *C09K 19/08* | (2006.01) | |
| *C09K 19/10* | (2006.01) | |
| *C09K 19/12* | (2006.01) | |
| *C09K 19/18* | (2006.01) | |
| *C07C 13/47* | (2006.01) | |

(52) U.S. Cl.
CPC .......... *C09K 19/3059* (2013.01); *C07C 13/47* (2013.01); *C09K 19/08* (2013.01); *C09K 19/10* (2013.01); *C09K 19/12* (2013.01); *C09K 19/18* (2013.01); *C09K 19/322* (2013.01); *C09K 2019/183* (2013.01); *C09K 2219/11* (2013.01)

(58) Field of Classification Search
CPC ........ C09K 19/18; C09K 19/08; C09K 19/10; C09K 19/12; C09K 19/322; C07C 13/47
See application file for complete search history.

(56) References Cited

U.S. PATENT DOCUMENTS

| | | | |
|---|---|---|---|
| 6,149,837 A | 11/2000 | Sekine et al. | |
| 6,623,810 B2 | 9/2003 | Sekine et al. | |
| 7,255,811 B2 | 8/2007 | Hirschmann et al. | |
| 7,361,288 B2 | 4/2008 | Lussem et al. | |
| 7,419,706 B2 * | 9/2008 | Heckmeier | C09K 19/32 252/299.61 |
| 8,129,002 B2 * | 3/2012 | Kirsch | 252/299.01 |
| 8,557,142 B2 * | 10/2013 | Montenegro et al. | 252/299.63 |
| 8,747,695 B2 | 6/2014 | Jasper | |
| 2001/0050353 A1 | 12/2001 | Sekine et al. | |
| 2004/0236138 A1 | 11/2004 | Hirschmann et al. | |
| 2005/0067605 A1 | 3/2005 | Lussem et al. | |
| 2010/0073621 A1 * | 3/2010 | Shimada | C09K 19/10 349/182 |
| 2011/0007260 A1 * | 1/2011 | Chien | C09K 19/02 349/186 |
| 2012/0205583 A1 | 8/2012 | Montenegro et al. | |
| 2012/0273724 A1 | 11/2012 | Jasper et al. | |
| 2013/0221274 A1 * | 8/2013 | Reiffenrath et al. | 252/299.63 |
| 2013/0277611 A1 | 10/2013 | Jasper et al. | |
| 2013/0292608 A1 * | 11/2013 | Manabe et al. | 252/299.63 |

FOREIGN PATENT DOCUMENTS

| | | |
|---|---|---|
| CN | 1572758 A | 2/2005 |
| CN | 102574754 A | 7/2012 |
| CN | 102575165 A | 7/2012 |
| CN | 103298910 A | 9/2013 |
| DE | 10120024 A1 | 11/2001 |
| DE | 102004029429 A1 | 2/2005 |
| GB | 2367057 A * | 3/2002 |
| JP | 05-255151 A | 10/1993 |
| JP | 2701083 B2 * | 1/1998 |
| JP | 10-045642 A | 2/1998 |
| JP | 11-158094 A | 6/1999 |
| JP | 2001072977 A | 3/2001 |
| JP | 2002338518 A | 11/2002 |
| JP | 2003-055664 A | 2/2003 |
| JP | 3569935 B2 | 7/2004 |

(Continued)

OTHER PUBLICATIONS

Translation of JP2005120208.*
Translation of WO2009125721.*
Translation of JP2006276649.*
Lim et al. "Liquid Crystal Millimeter Wave Electronic Phase Shifter" Mar. 8, 1993, Applied Physics Letters, vol. 62 No. 10, 1065-1067.*
English Translation of JP2701083.*
Official Action related to corresponding Chinese Patent Application No. 2012-80014270.7 dated Sep. 18, 2014.
International Search Report from PCT/EP2012/000828 dated May 4, 2012.

(Continued)

*Primary Examiner* — Cynthia H Kelly
*Assistant Examiner* — Anna Malloy
(74) *Attorney, Agent, or Firm* — Millen White Zelano and Branigan, PC; Csaba Henter; Anthony Zelano

(57) ABSTRACT

Compounds containing at least one C—C triple bond within a chain of at least 3 ring systems which have positive dielectric anisotropy, the use thereof for high-frequency components, liquid-crystalline media containing these compounds, and high-frequency components, in particular antennae, especially for the gigahertz region, containing these media. The liquid-crystalline media serve, for example, for the phase shifting of microwaves for tuneable phased-array antennae.

20 Claims, No Drawings

(56) References Cited

FOREIGN PATENT DOCUMENTS

| JP | 2005-120208 A | | 5/2005 |
|---|---|---|---|
| JP | 3858283 B2 | | 9/2006 |
| JP | 2006276649 A | * | 10/2006 |
| JP | 3900554 B2 | | 1/2007 |
| JP | 2007320985 A | | 12/2007 |
| TW | 1490315 B | | 7/2015 |
| WO | 2009125721 A1 | | 10/2009 |
| WO | 2011047781 A1 | | 4/2011 |

OTHER PUBLICATIONS

Sebastian Gauza et al. "Physical Properties of Laterally Fluorinated Isothiocyanato Phenyl-tolane Single Liquid Crystals Components and Mixtures" Molecular Crystals and Liquid Crystals, vol. 489, No. 1, [Jan. 2008], pp. 135/[461]-147[473].

G. W. Gray et al. "Mesomorphic Transition Temperatures for the Homologous Series of 4-n-Alkyl-4'-Cyanotolanes and Other Related Compounds" Molecular Crystals and Liquid Crystals, vol. 37, No. 1, [1976], pp. 213-231.

Gong Xin He et al. "Syntheses and Thermal Properties of New Liquid Crystals Bearing a Crown Ether Ring: Cation Binding in the Nematic Phase1" The Journal of Organic Chemistry, vol. 55, No. 2, [1990], pp. 541-548.

Shin-Tson Wu et al. "Physical Properties of Polar Bis-Tolane Liquid Crystals" Jpn. J. Appl. Phys., vol. 39, [2000], pp. L38-L41.

Shin-Tson Wu et al. "RoomTemperature Bis-tolane Liquid Crystals" Jpn. J. Appl. Phys., vol. 38, [1999], pp. L286-L288.

Official Action related to corresponding Chinese Patent Application No. 2012-80014270.7 dated Apr. 3, 2015.

Akiyama, Shuzo et al., "Direct C C Triple Bond Formation form the C C Double Bond with Potassium tert-Butoxide in Dimethylformamide containing Trace Amounts of Oxygen", J. Chem. Soc., Chem. Commun., 1991—pp. 948-950.

Dubois, Frederic, et al., "Large Microwave Birefringence Liquid-Crystal Characterization for Phase-Shifter Applications", Japanese Journal of Applied Physics, vol. 47, No. 5, 2008, pp. 3564-3567.

Wu, Shin-Tson et al., "High birefringence and wide nematic range bis-tolane liquid crystals", Applied Physics Letters, vol. 74, No. 3, Jan. 18, 1999, pp. 344-346.

Search Report relating to Taiwan Patent Application No. 101110269 dated Sep. 15, 2015.

* cited by examiner

COMPOUNDS HAVING A C—C TRIPLE BOND

The present invention relates to compounds containing at least one C—C triple bond within a chain of at least 3 ring systems which have positive dielectric anisotropy, to the use thereof for high-frequency components, to liquid-crystalline media comprising the compounds, and to high-frequency components, in particular antennae, especially for the gigahertz region, comprising these media. The liquid-crystalline media serve, for example, for the phase shifting of microwaves for tuneable 'phased-array' antennae.

Liquid-crystalline media have been used for some time in electro-optical displays (liquid crystal displays—LCDs) in order to display information.

However, liquid-crystalline media have recently also been proposed for use in components for microwave technology, such as, for example, in DE 10 2004 029 429 A and in JP 2005-120208 (A).

An industrially valuable application of liquid-crystalline media in high-frequency technology is based on their property that their dielectric properties can be controlled by a variable voltage, particularly for the gigahertz region. Thus, tuneable antennae can be designed which contain no moving parts (A. Gaebler, A. Moessinger, F. Goelden, et al., "Liquid Crystal-Reconfigurable Antenna Concepts for Space Applications at Microwave and Millimeter Waves", International Journal of Antennas and Propagation, Vol. 2009, Article ID 876989, 7 pages, 2009. doi:10.1155/2009/876989).

The publication A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, 545-548, describes, inter alia, the properties of the known, liquid-crystalline single substance K15 (Merck KGaA, Germany) at a frequency of 9 GHz.

DE 10 2004 029 429 A (cf. above) describes the use of conventional liquid-crystal media in microwave technology, inter alia in phase shifters. Liquid-crystalline media have already been investigated therein with respect to their properties in the corresponding frequency range.

Compounds containing a C—C triple bond within a chain of 4 benzene rings arranged in a linear manner are disclosed in the specifications JP 05-255151 A and WO 2009/125721 A1. Some of the compounds from JP 05-255151 A are provided with fluorine substituents and are used as a component of liquid-crystalline media. The compounds disclosed in the second specification are only substituted at the ends of the molecule and serve as a constituent of thin-film transistors.

Liquid-crystalline compounds having very high optical anisotropy and clearly positive values of the dielectric anisotropy are rare to date. Compounds of this type are certain bistolans containing a polar end group, as disclosed, for example, in the publications Shin-Tson Wu et al. Jpn. J. Appl. Phys. 1999, 38, 286-288, Shin-Tson Wu et al. Jpn. J. Appl. Phys. 2000, 39, 38-41, JP 10-45642 A and DE 10120024.

However, the compositions or individual compounds known to date are generally afflicted with disadvantages. Most of them result, besides other deficiencies, in disadvantageously high losses and/or inadequate phase shifts or inadequate material quality. Whereas, for example, some individual compounds do not have favourable liquid-crystalline phases and have very high melting points, other substances in turn lack sufficiently high values of Δn and.

For use in high-frequency technology, liquid-crystalline media having particular, to date rather unusual, non-standard properties, or combinations of properties, are required.

Thus, novel components for liquid-crystalline media having improved properties are necessary. In particular, the loss in the microwave range must be reduced and the material quality (η) must be improved. Furthermore, applications in antenna technology take place under in some cases strongly varying outside boundary conditions, such as, for example, large temperature variations. In particular, there is a need to improve the low-temperature behaviour of the components.

There is therefore a considerable demand for liquid-crystalline media having suitable properties for corresponding practical applications.

Surprisingly, it has been found that the compounds according to the invention have low melting points and high clearing points (transition from the nematic phase into the isotropic phase). In the liquid-crystalline range, the compounds are predominantly nematic or support the nematic phase. At the same time, the optical anisotropy (Δn) and the dielectric anisotropy ( ) are equally at high positive values, making them highly suitable, for example, for use as high-frequency medium. It has been found that, with the compounds according to the invention, it is possible to achieve liquid-crystalline media having a broad nematic phase range, at the same time high values of Δn and, and advantageous high-frequency properties.

The invention relates to compounds of the formula I,

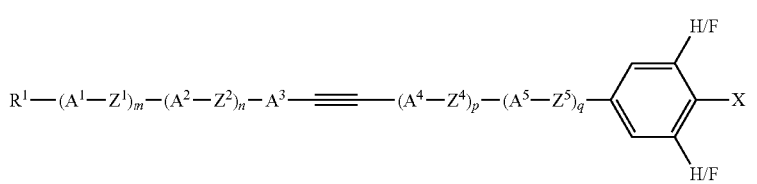

in which

A$^{1-5}$, independently of one another, optionally oriented to both sides, denote a) 1,4-phenylene, in which one or more, preferably one to two, CH groups may be replaced by N, b) a radical of the formula

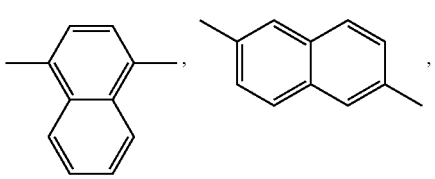

-continued

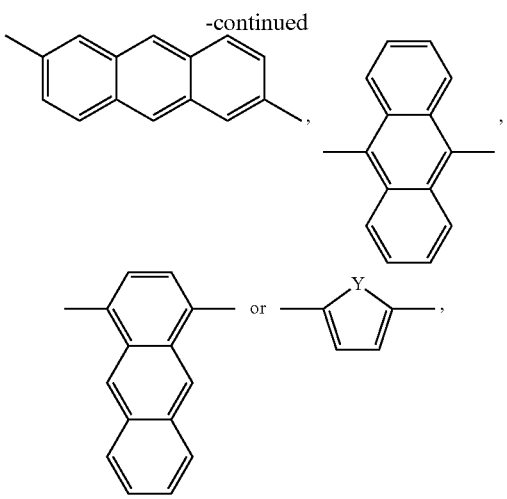

in which Y denotes S or O,
c) trans-1,4-cyclohexylene or cyclohexenylene, in which, in addition, one or two non-adjacent CH$_2$ groups may be replaced by —O— and/or —S—, and in which H may be replaced by F, or
d) a radical from the group 1,4-bicyclo[2.2.2]octylene, cyclobutane-1,3-diyl, spiro[3.3]heptane-2,6-diyl, thiophene-2,4-diyl or furan-2,4-diyl,
and in which, in groups a), b), c) and d),
optionally one or more H atoms independently have been replaced by a group L,
where at least the ring A$^3$ and/or the ring A$^4$ where p=1 denote(s) a radical selected from the radicals

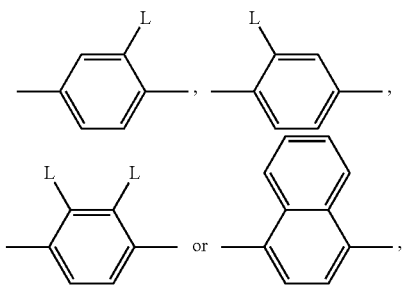

L denotes Br, Cl, F, CN, —NCS, —SCN, SF$_5$, C$_1$-C$_{10}$ alkyl, C$_1$-C$_{10}$ alkoxy, C$_3$-C$_6$ cycloalkyl or a mono- or polyfluorinated C$_1$-C$_{10}$ alkyl or alkoxy group,
R$^1$ in each case, independently of one another, denotes a halogenated or unsubstituted alkyl radical having 1 to 15 C atoms, where, in addition, one or more CH$_2$ groups in these radicals may each be replaced, independently of one another, by —C≡C—, —CH═CH—, —CF═CF—, —CF═CH—, —CH═CF—, —(CO)O—, —O(CO)—, —(CO)—, —O— or —S— in such a way that O or S atoms are not linked directly to one another,
or F, Cl, Br, CN, CF$_3$, OCF$_3$, SCN, NCS or SF$_5$,
X denotes F, Cl, Br, CN, SCN, NCS, SF$_5$ or a halogenated alkyl radical having 1 to 15 C atoms, where, in addition, one or more CH$_2$ groups in this radical may each be replaced, independently of one another, by —C≡C—, —CH═CH—, —CF═CF—, —CF═CF—, —CH═CF—, —(CO)O—, —O(CO)—, —(CO)—, —O— or —S— in such a way that O or S atoms are not linked directly to one another, Z$^1$, Z$^2$, Z$^4$, Z$^5$, independently of one another, denote a single bond, —C≡C—, —CH═CH—, —CH$_2$O—, —(CO)O—, —CF$_2$O—, —CF$_2$CF$_2$—, —CH$_2$CF$_2$—, —CH$_2$CH$_2$—, —(CH$_2$)$_4$—, —CH═CF— or —CF═CF—, where asymmetrical bridges may be oriented to both sides, and
m, n, p, q independently denote 0 or 1, where m+n+p+q is 1, 2, 3 or 4, preferably 1, 2 or 3, particularly preferably 1 or 2.

The optional double bonds of the formula —C(H/F)═CF— in the groups Z$^{1/2/4/5}$ between the rings A$^1$ to A$^5$ preferably have the trans configuration (E configuration).

The compounds according to the invention have a comparatively very low melting point, a high clearing point, high optical anisotropy (Δn) and clearly positive dielectric anisotropy. The undesired rotation of the compounds is restricted, making them particularly suitable for use in the gigahertz region. The relatively low loss factor in the microwave spectrum is advantageous. The compounds have, alone or in a mixture with further mesogenic components, a nematic phase over a broad temperature range. The totality of these properties make them particularly suitable for use in components for high-frequency technology, in particular in liquid-crystalline phase shifters. Liquid-crystalline media according to the invention have the corresponding properties.

Preferred compounds of the formula I are characterised by the choice of one or more of the following parameters:

The index p is particularly preferably 1. The sum of the indices m+n is preferably 0 or 1, particularly preferably 0. The sum of the indices p+q is preferably 0, 1 or 2, particularly preferably 2. The total number of ring systems in formula I is therefore 2+m+n+p+q, preferably 3, 4, 5 or 6, particularly preferably 3, 4 or 5, and in particular 4.

The groups A$^1$, A$^2$, A$^3$, A$^4$ and A$^5$ preferably include ring groups in accordance with definition a), b) or c), particularly preferably ring groups in accordance with definition a) or b), and very particularly preferably in accordance with definition a).

The ring groups in accordance with definition a) preferably have the part-structure

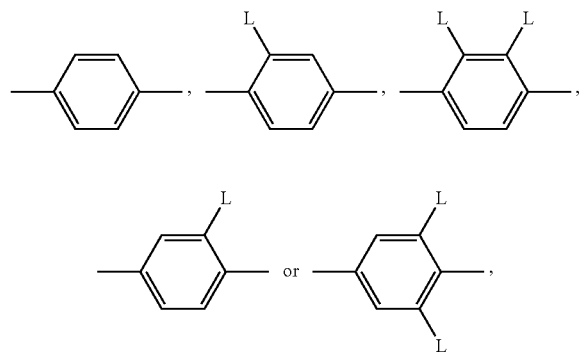

in which L independently denotes Br, Cl, F, CN, —NCS, —SCN, SF$_5$, C$_1$-C$_{10}$ alkyl, C$_1$-C$_{10}$ alkoxy, C$_3$-C$_6$ cycloalkyl or a mono- or polyfluorinated C$_1$-C$_{10}$ alkyl or alkoxy group.

The group A³ preferably has a part-structure selected from the following formulae:

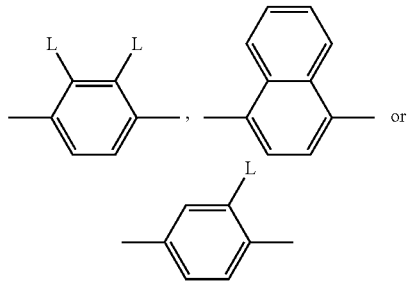

and/or
the group A⁴, if present (p=1), preferably has a part-structure selected from the following formulae:

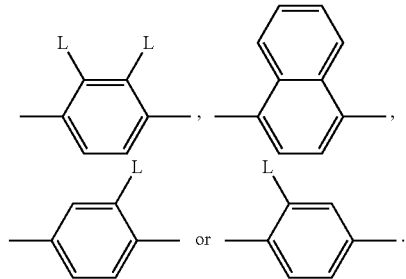

Particularly preferred part-structures "-A³-≡-A⁴-" here are selected from the following part-structures:

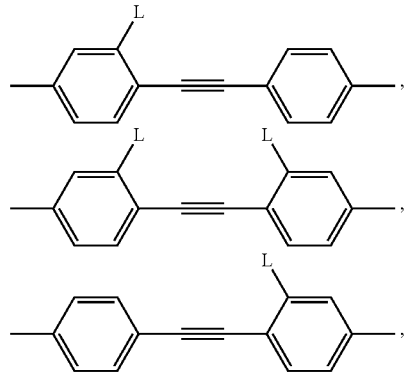

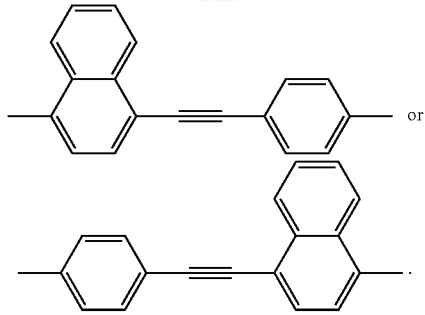

Preferred compounds of the formula I are those in which the head group is a group selected from the following formulae:

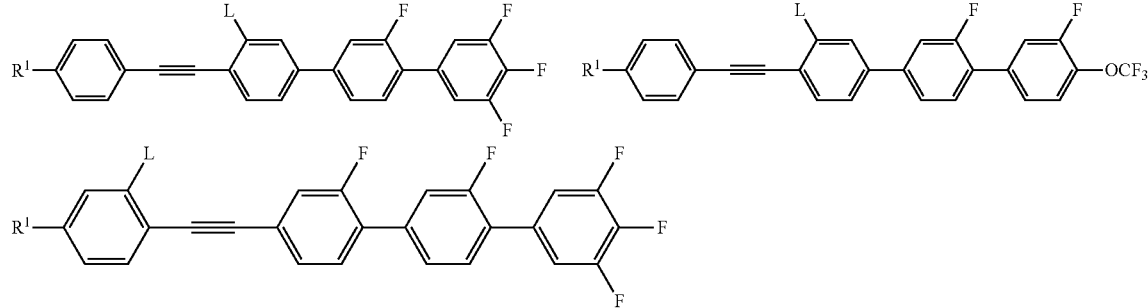

The bridging groups $Z^{1/2/4/5}$ are preferably, independently of one another, a single bond, —C≡C—, —CF=CF— or —CH=CH—, particularly preferably a single bond.

$R^1$ preferably denotes a straight-chain alkyl radical having 1 to 15 C atoms, where, in addition, one or more $CH_2$ groups in these radicals may each be replaced, independently of one another, by —C≡C—, —CH=CH—, —(CO)O—, —O(CO)—, —(CO)—, —O— in such a way that O atoms are not linked directly to one another. The group $R^1$ is preferably an alkyl radical having 2 to 7 C atoms.

The group X preferably denotes F, Cl, Br, CN, $CF_3$, $OCF_3$, SCN, NCS, $SF_5$ or a (different) halogenated alkyl radical having 1 to 7 C atoms, where, in addition, one or more $CH_2$ groups in this radical may each be replaced, independently of one another, by —C≡C—, —CH=CH—, —CF=CF—, —CF=CH—, —CH=CF—, —(CO)O—, —O(CO)—, —(CO)—, —O— or —S—. The group X particularly preferably denotes F, Cl, Br, CN, NCS, SCN, $SF_5$, fluorinated alkyl or fluorinated alkoxy having 1 to 7 C atoms (for example $CF_3$ or $OCF_3$) or fluorinated alkenyl, fluorinated alkenyloxy (for example —OCF=$CF_2$) or fluorinated alkoxyalkyl having 2 to 7 C atoms, very particularly preferably fluorinated alkoxy, fluorinated alkenyloxy, F or Cl.

The group L preferably denotes methyl, ethyl, propyl, cyclopropyl or Cl.

Preferred embodiments of the invention are therefore represented by the following illustrative structures:

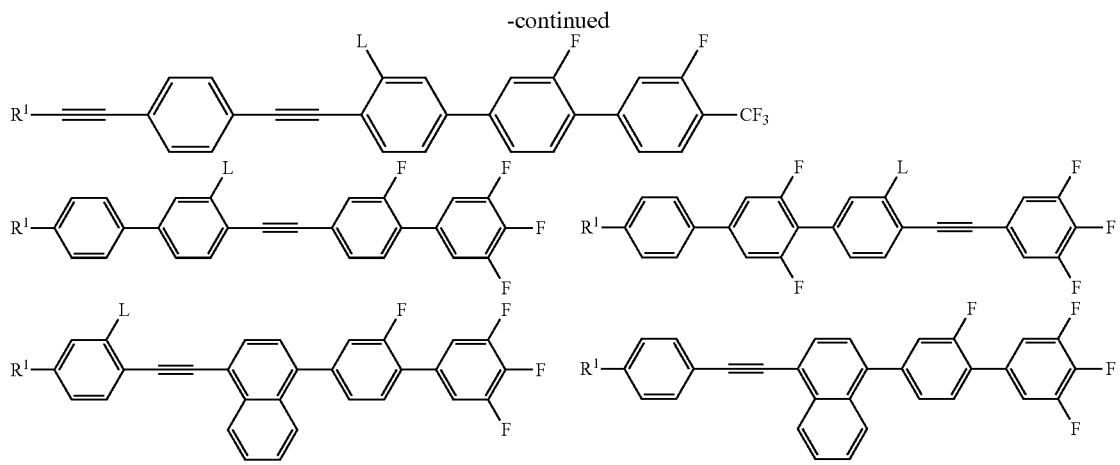

in which $R^1$ is as defined in formula I, and in particular $R^1$ denotes an alkyl radical having 2 to 7 C atoms, for example a propyl radical or a butyl, pentyl or hexyl radical.

The compounds of the formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Typical compounds of the formula I can advantageously be prepared as evident from the following illustrative synthesis schemes (Scheme 1):

$R^1$ in Scheme 1 has the meaning of $R^1$ as defined for formula I. Reaction Scheme 1 shows the synthesis of certain compounds. The phenyl radicals "$R^1$-phenyl" can be generalised here to any desired radicals "$R^1$-$(A^1$-$Z^1)_m$-$(A^2$-$Z^2)_n$-$A^3$-" in accordance with formula I. The other rings can likewise be varied in type and substitution in accordance with formula I. The parameters L and X are as defined above and below.

The liquid-crystalline media in accordance with the present invention comprise one or more compounds of the formula I and optionally at least one further, preferably mesogenic compound. The liquid-crystal medium therefore preferably comprises two or more compounds which are preferably liquid-crystalline. Preferred media comprise the preferred compounds of the formula I.

Scheme 1: Synthesis scheme for the preparation of compounds of the formula I in which m + n = 0 and p + q = 2.

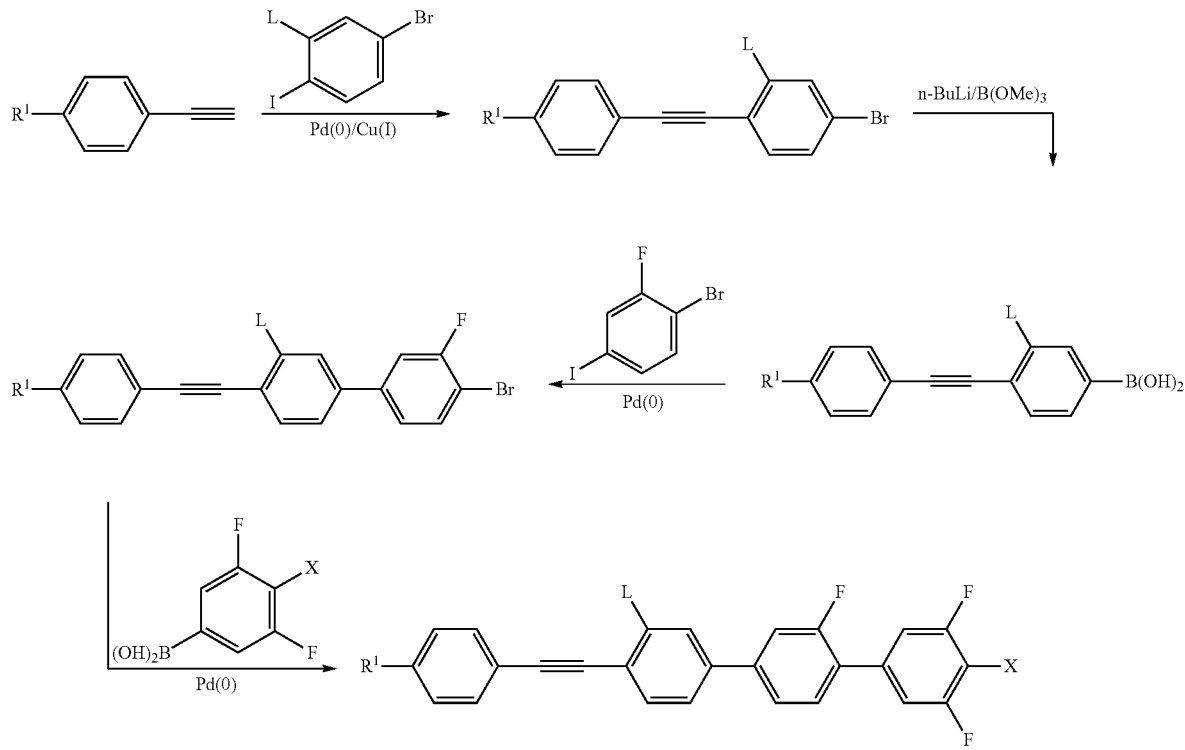

Further components of the liquid-crystalline media are preferably selected from the compounds of the formula II:

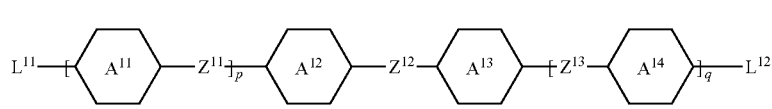

in which
$L^{11}$ denotes $R^{11}$ or $X^{11}$,
$L^{12}$ denotes $R^{12}$ or $X^{12}$,
$R^{11}$ and $R^{12}$, independently of one another, denote unfluorinated alkyl or unfluorinated alkoxy having 1 to 17, preferably having 3 to 10, C atoms or unfluorinated alkenyl, unfluorinated alkynyl, unfluorinated alkenyloxy or unfluorinated alkoxyalkyl having 2 to 15, preferably 3 to 10, C atoms, preferably alkyl or unfluorinated alkenyl,
$X^{11}$ and $X^{12}$, independently of one another, denote F, Cl, Br, CN, NCS, SCN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl,
p, q independently denote 0 or 1,
$Z^{11}$ to $Z^{13}$, independently of one another, denote trans-CH=CH—, trans-CF=CF—, —C≡C— or a single bond, and

to

independently of one another, denote

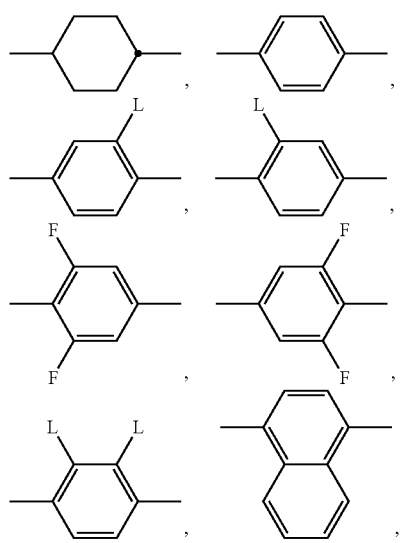

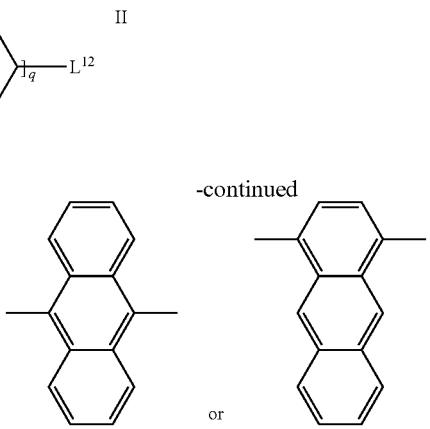

in which L independently denotes branched or unbranched alkyl, alkenyl or alkynyl having 1 to 12 C atoms, in which, independently of one another, one or more "—$CH_2$—" groups may also be replaced by O, or denotes $C_3$-$C_6$ cycloalkyl, $C_3$-$C_6$ cycloalkenyl, fluorinated alkyl or alkenyl, fluorinated alkoxy or alkenyloxy,
F, Cl, Br, CN, NCS, SCN or $SF_5$.

In a preferred embodiment of the present invention, the liquid-crystalline media comprise one or more compounds of the formula I and one or more compounds of the formula II.

The liquid-crystalline media in accordance with the present application preferably comprise in total 5 to 95%, preferably 10 to 90% and particularly preferably 15 to 80%, of compounds of the formula I.

The liquid-crystalline media in accordance with the present invention preferably comprise, more preferably predominantly consist of, even more preferably essentially consist of and very preferably completely consist of compounds selected from the group of the compounds of the formulae I and II.

In this application, "comprise" in connection with compositions means that the entity in question, i.e. the medium or the component, comprises the component or components or compound or compounds indicated, preferably in a total concentration of 10% or more and very preferably 20% or more.

In this connection, "predominantly consist of" means that the entity in question comprises 55% or more, preferably 60% or more and very preferably 70% or more, of the component or components or compound or compounds indicated.

In this connection, "essentially consist of" means that the entity in question comprises 80% or more, preferably 90% or more and very preferably 95% or more, of the component or components or compound or compounds indicated.

In this connection, "completely consist of" means that the entity in question comprises 98% or more, preferably 99% or more and very preferably 100.0%, of the component or components or compound or compounds indicated.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants and nanoparticles. The individual, added compounds are employed in concentrations of 0.005 to 6%, preferably 0.1 to 3%. The total concentration of these further constituents is in the range from 0% to 10%, preferably 0.1% to 6%, based on the mixture as a whole. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethyl-piperidines or 2-benzotriazol-2-ylphenols. These assistants are known to the person skilled in the art and are commercially available, for example as light stabilisers.

An embodiment of the invention is therefore also a process for the preparation of a liquid-crystal medium which is characterised in that one or more compounds of the formula I are mixed with one or more further compounds and optionally with one or more additives. The further compounds are preferably selected from the compounds of the formula II, as indicated above, and optionally one or more further compounds.

In the present application, the expression dielectrically positive describes compounds or components where $\Delta\epsilon > 3.0$, dielectrically neutral describes those where $-1.5 \leq \Delta\epsilon \leq 3.0$ and dielectrically negative describes those where $\Delta\epsilon < -1.5$. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

$\Delta\epsilon$ is defined as $(\epsilon_\parallel - \epsilon_\perp)$, while $\epsilon_{average}$ is $(\epsilon_\parallel + 2\epsilon_\perp)/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest.

The values are extrapolated to a concentration of the compounds of interest of 100%.

Components having a nematic phase at the measurement temperature of 20° C. are measured as such, all others are treated like compounds.

The term threshold voltage in the present application refers to the optical threshold and is quoted for 10% relative contrast ($V_{10}$), and the term saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties that are typical for liquid crystals are determined in accordance with "Merck Liquid Crystals, Physical Properties of Liquid Crystals", status November 1997, Merck KGaA, Germany, and are quoted for a temperature of 20° C., unless expressly stated otherwise. The optical anisotropy ($\Delta n$) is determined at a wavelength of 589.3 nm. The dielectric anisotropy ($\Delta\epsilon$) is determined at a frequency of 1 kHz. The threshold voltages, as well as all other electro-optical properties, are determined using test cells produced at Merck KGaA, Germany. The test cells for the determination of $\Delta\epsilon$ have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\epsilon_\parallel$) and polyimide AL-1054 from Japan Synthetic Rubber, Japan, for homogeneous orientation ($\epsilon_\perp$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages are determined under perpendicular observation. The threshold ($V_{10}$), mid-grey ($V_{50}$) and saturation ($V_{90}$) voltages are determined for 10%, 50% and 90% relative contrast respectively.

The liquid-crystalline media are investigated with respect to their properties in the microwave frequency range as described in A. Penirschke et al. "Cavity Perturbation Method for Characterization of Liquid Crystals up to 35 GHz", 34$^{th}$ European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an internal radius of 180 μm and an external radius of 350 μm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the result of the output signal is recorded using a commercial vector network analyser. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnet is set correspondingly and then rotated correspondingly through 90°.

The dielectric anisotropy in the microwave region is defined as $$\Delta\epsilon_r = (\epsilon_{r,\parallel} - \epsilon_{r,\perp}).$$

The modulatability or tuneability ($\tau$) is defined as $$\tau = (\Delta\epsilon_r / \epsilon_{r,\parallel}).$$

The material quality ($\eta$) is defined as $$\eta = (\tau / \tan \delta_{\epsilon,r,max}),$$

with the maximum dielectric loss factor $\tan \delta_{\epsilon,r,max}$:
$\tan \delta_{\epsilon r,max} = \max. \{\tan \delta_{\epsilon r, \perp}; \tan \delta_{\epsilon r,\parallel}\}$
which arises from the maximum value of the measured values for $\tan \delta_{\epsilon r}$.

The material quality ($\eta$) of the preferred liquid-crystal materials is 6 or more, preferably 7 or more, preferably 10 or more, preferably 15 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

The liquid-crystal media according to the invention preferably have nematic phases of in each case at least from −20° C. to 80° C., preferably from −30° C. to 85° C. and very particularly preferably from −40° C. to 100° C. The phase particularly preferably extends to 120° C. or more, preferably to 140° C. or more and very particularly preferably to 180° C. or more. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a cell thickness of 5 µm for at least 100 hours. At high temperatures, the clearing point is measured in capillaries by conventional methods.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The $\Delta\epsilon$ of the liquid-crystal medium in accordance with the invention, at 1 kHz and 20° C., is preferably 1 or more, more preferably 2 or more and very preferably 3 or more.

The $\Delta n$ of the liquid-crystal media in accordance with the present invention, at 589 nm ($Na^D$) and 20° C., is preferably in the range from 0.20 or more to 0.90 or less, more preferably in the range from 0.25 or more to 0.90 or less, even more preferably in the range from 0.30 or more to 0.85 or less and very particularly preferably in the range from 0.35 or more to 0.80 or less.

In a preferred embodiment of the present application, the $\Delta n$ of the liquid-crystal media in accordance with the present invention is preferably 0.50 or more, more preferably 0.55 or more.

Furthermore, the liquid-crystal media according to the invention are characterised by high anisotropies in the microwave region. The birefringence is, for example, preferably 0.14 or more, particularly preferably 0.15 or more, particularly preferably 0.20 or more, particularly preferably 0.25 or more and very particularly preferably 0.30 or more, at about 8.3 GHz. In addition, the birefringence is preferably 0.80 or less.

The liquid crystals employed are either single substances or mixtures. They preferably have a nematic phase.

In the present application, the term compounds means both one compound and a plurality of compounds, unless expressly stated otherwise.

Preferred components which comprise a liquid-crystal medium or at least one compound in accordance with the invention are phase shifters, varactors, antenna arrays (for example for radio, mobile communications, microwave/radar and other data transmission), 'matching circuit adaptive filters' and others. Preference is given to components for high-frequency technology, as defined above. Preference is also given to components which can be modulated by different applied electrical voltages. Very particularly preferred components are tuneable phase shifters. In preferred embodiments, a plurality of phase shifters are functionally connected, giving, for example, a phase-controlled group antenna, generally referred to as 'phased array' antenna. A group antenna uses the phase shift of the transmitting or receiving elements arranged in a matrix in order to achieve bundling through interference. A parallel arrangement of phase shifters in row or grid form enables the construction of a so-called 'phased array', which can serve as tuneable or passive transmitting or receiving antenna for high frequencies (for example gigahertz region). Phased-array antennae according to the invention have a very broad usable reception cone.

Preferred applications are radar installations and data transmission equipment on manned or unmanned vehicles from the automobile, shipping, aircraft, space travel and satellite technology areas.

For the production of suitable components for high-frequency technology, in particular suitable phase shifters, a liquid-crystalline medium according to the invention is typically introduced into rectangular cavities having a thickness of less than 1 mm, a width of several millimeters and a length of several centimeters. The cavities have opposing electrodes mounted along two long sides. Such arrangements are familiar to the person skilled in the art. Through application of a variable voltage, the dielectric properties of the liquid-crystalline medium can be tuned during operation of the antenna in order to set different frequencies or directions of an antenna.

The expression "halogen" or "halogenated" stands for F, Cl, Br and I, particularly for F and Cl and in particular for F. A halogenated alkyl radical therefore preferably means a chlorinated or fluorinated alkyl radical.

The expression "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The expression "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The expression "alkoxy" preferably encompasses straight-chain radicals of the formula $C_nH_{2n+1}$—O—, in which n denotes 1 to 10. n is preferably 1 to 6. Preferred alkoxy groups are, for example, methoxy, ethoxy, n-propoxy, n-butoxy, n-pentoxy, n-hexoxy, n-heptoxy, n-octoxy, n-nonoxy, n-decoxy.

The expression "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

The expression "fluorinated alkyl radical" preferably encompasses mono- or polyfluorinated radicals. Perfluorinated radicals are included. Preference is given to $CF_3$, $CH_2CF_3$, $CH_2CHF_2$, $CHF_2$, $CH_2F$, $CHFCF_3$ and $CF_2CHFCF_3$, particularly preferably $CF_3$.

The expression "fluorinated alkoxy radical" encompasses mono- or polyfluorinated radicals. Perfluorinated radicals are preferred. Particular preference is given to the $OCF_3$ radical.

The expression "alk(en/yn)yl groups, in which one or more "—$CH_2$—" groups may be replaced by —O—" preferably relates to groups of this type in which a non-terminal $CH_2$ group is replaced. OH groups are included in the general meaning.

The expression "substituted cycloalkyl" encompasses cycloalkyl which is mono- or polysubstituted by alkyl, in particular alkyl having 1 to 8 carbon atoms.

The expression "substituted phenyl" encompasses phenyl which is mono- or polysubstituted by a group defined like $R^1$, in particular phenyl which is substituted by F, Cl, alkyl or alkoxy.

In the present application, high-frequency technology means applications having frequencies in the range from 1 MHz to 10 THz, preferably from 1 GHz to 3 THz, more preferably from 2 GHz to 1 THz, particularly preferably from 5 to 300 GHz. The application is preferably in the microwave spectrum or adjacent regions which are suitable for message transmission, in which phased-array modules can be used in transmitting or receiving antennae.

The liquid-crystal media according to the invention consist of one or more compounds, preferably 2 to 30, more preferably 3 to 20 and very preferably 3 to 16, compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present application and in the following examples, the structures of the liquid-crystal compounds are indicated by means of acronyms, where the transformation into chemical formulae is carried out in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
| --- | --- | --- | --- | --- |
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nN.F.F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF.F | $C_nH_{2n+1}$ | F | F | H |
| nF.F.F | $C_nH_{2n+1}$ | F | F | F |
| $nOCF_3$ | $C_nH_{2n+1}$ | $OCF_3$ | H | H |
| $nOCF_3$.F | $C_nH_{2n+1}$ | $OCF_3$ | F | H |
| n-Vm | $C_nH_{2n+1}$ | —CH=CH—$C_mH_{2m+1}$ | H | H |
| nV-Vm | $C_nH_{2n+1}$—CH=CH— | —CH=CH—$C_mH_{2m+1}$ | H | H |

Suitable mixture components can be found in Tables A and B.
TABLE A
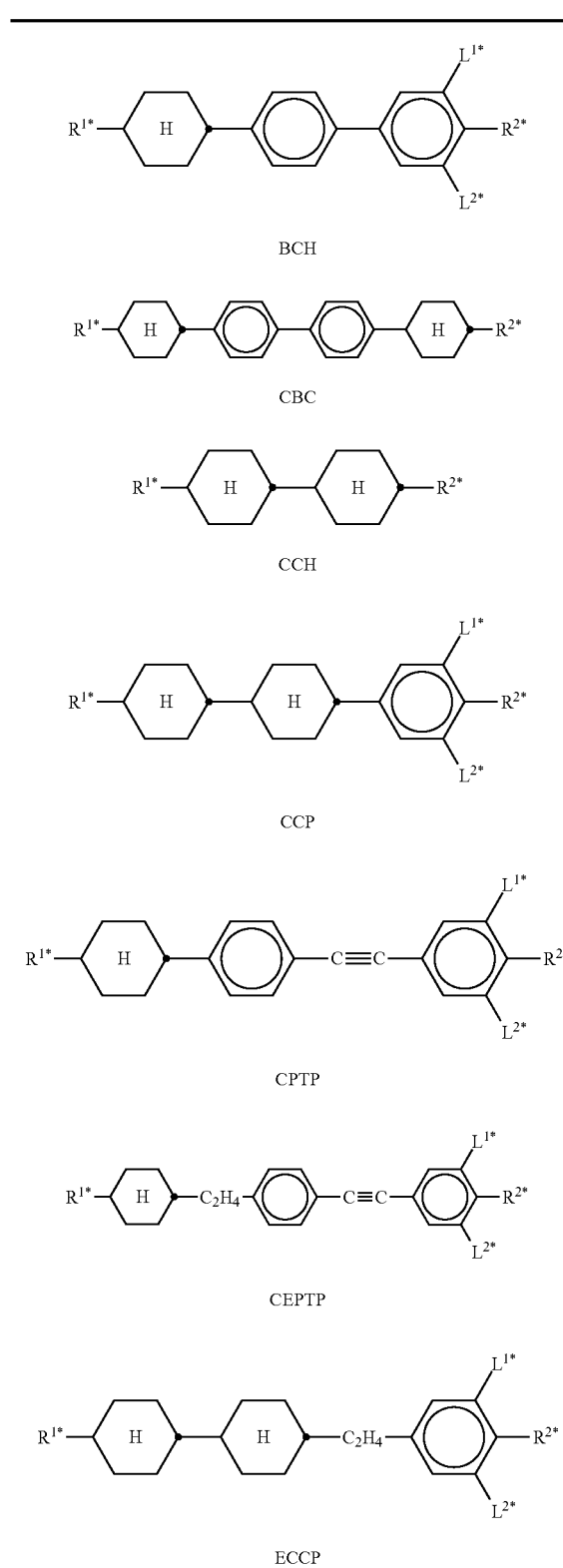
TABLE A-continued
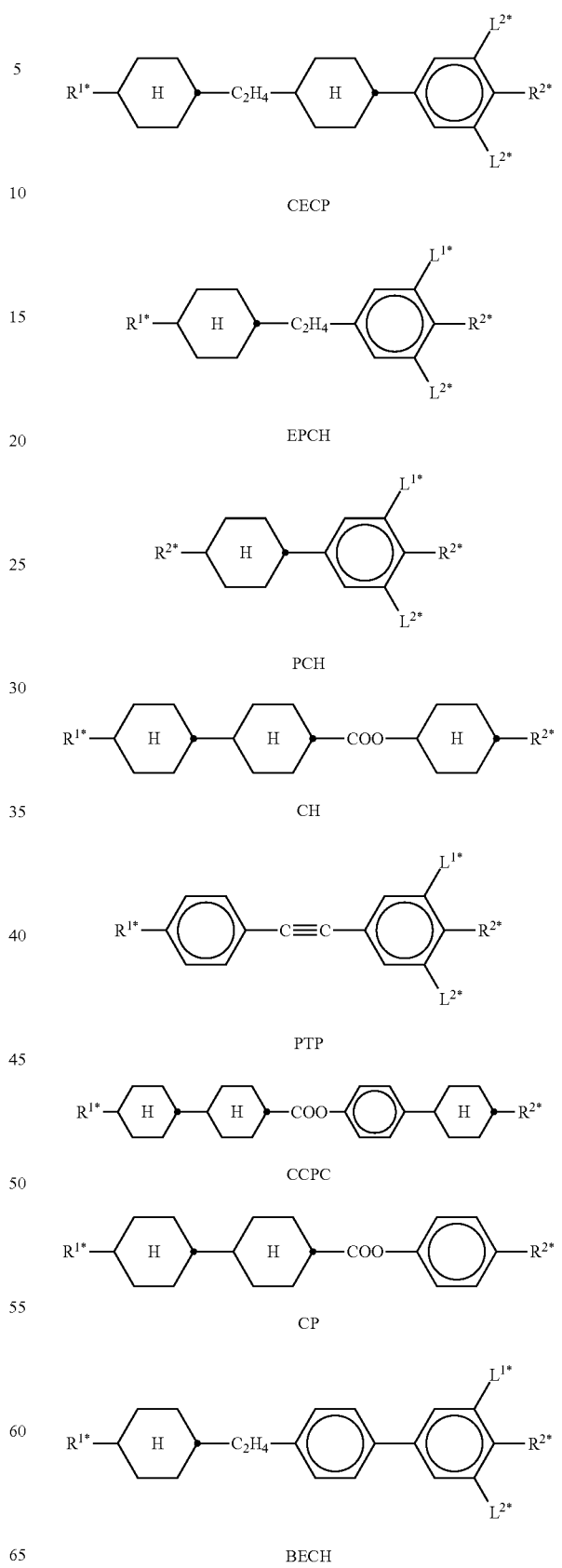

TABLE B

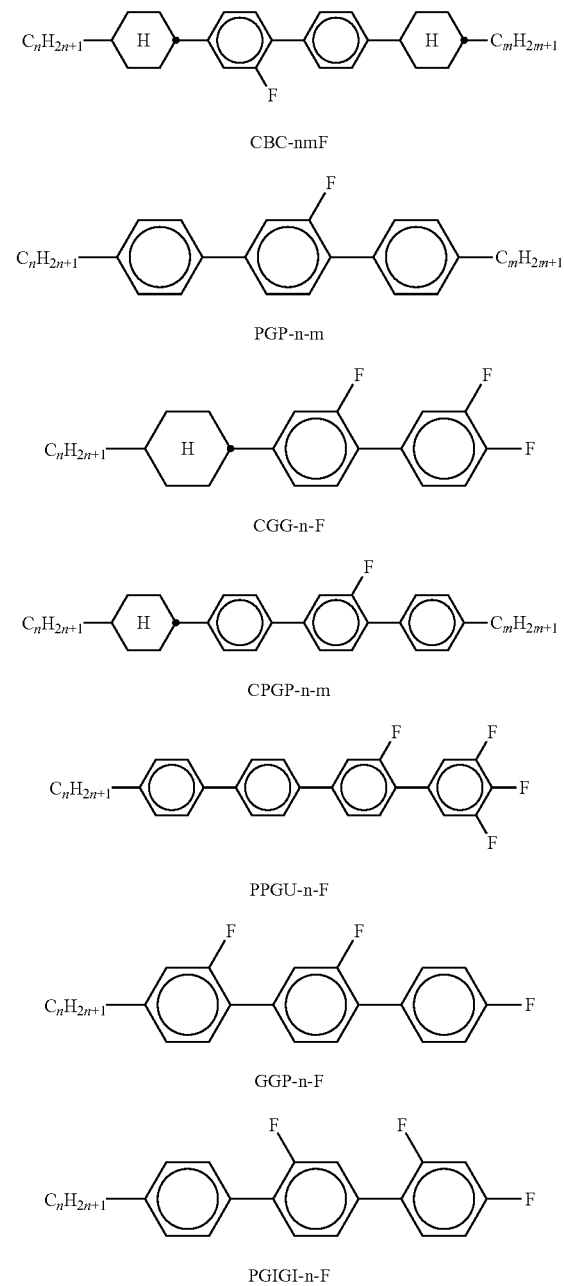

CBC-nmF

PGP-n-m

CGG-n-F

CPGP-n-m

PPGU-n-F

GGP-n-F

PGIGI-n-F

The following examples illustrate the present invention without limiting it in any way.

However, it becomes clear to the person skilled in the art from the physical properties what properties can be achieved and in what ranges they can be modified. In particular, the combination of the various properties which can preferably be achieved is thus well defined for the person skilled in the art.

In the present application, unless expressly stated otherwise, the plural form of a term denotes both the singular form and the plural form, and vice versa. Further combinations of the embodiments and variants of the invention in accordance with the description also arise from the attached claims.

Abbreviations Used

MTB methyl tert-butyl ether
$SiO_2$ silica gel
RT room temperature (about 20° C.)

EXAMPLES

The acetylenes and boronic acids employed are commercially available or can be prepared analogously to known syntheses which are known to the person skilled in the art. The radicals "$C_4H_9$" stand for unbranched n-butyl radicals. The same applies correspondingly to $C_3H_7$, $C_6H_{13}$, etc.

Synthesis Example 1

1.1 Synthesis of 1-bromo-3-ethyl-4-(4-n-butylphenylethynyl)benzene

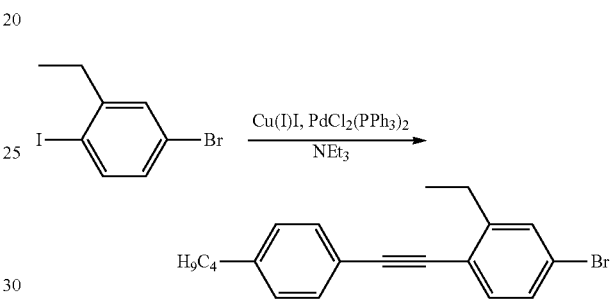

65 g (209 mmol) of 1-iodo-2-ethyl-4-bromobenzene and 38 g (226 mmol) of 4-n-butylphenylacetylene are initially introduced in 300 ml of $NEt_3$, 1 g (5.3 mmol) of copper(I) iodide and 3.6 g (5.1 mmol) of bis(triphenylphosphine) palladium(II) chloride are added, and the mixture is stirred at RT for 2 h. The batch is cooled, water and heptane are added, and the phases are separated. The organic phase is washed with saturated sodium chloride soln., dried over sodium sulfate, filtered and evaporated in a rotary evaporator. The residue is purified by column chromatography ($SiO_2$, heptane); the product is obtained as a colourless oil.

1.2 Synthesis of 3-ethyl-4-(4-n-butylphenylethynyl)phenylboronic acid

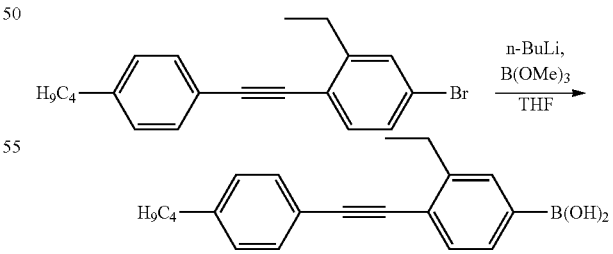

63 g (180 mmol) of the bromide obtained in the preceding reaction are initially introduced in 450 ml of tetrahydrofuran and cooled to −70° C., and 125 ml (1.6 M in hexane, 200 mmol) of n-butyllithium are added dropwise. After 1 h, 23 ml (203 mmol) of trimethyl borate in 50 ml of tetrahydrofuran are added, and the mixture is stirred at −70° C. for a further 2 h and warmed to 0° C. The mixture is then worked up using water and 1 M hydrochloric acid, MTB is added, the phases are separated, and the aqueous phase is extracted once with MTB. The combined organic phases are washed with saturated sodium chloride solution, dried over sodium sulfate, filtered and evaporated in a rotary evaporator. The residue is washed by stirring with heptane and filtered off. The boronic acid is obtained as a colourless solid.

1.3 Synthesis of 4-bromo-3-fluoro-3'-ethyl-4'-(4-n-butylphenylethynyl)biphenyl

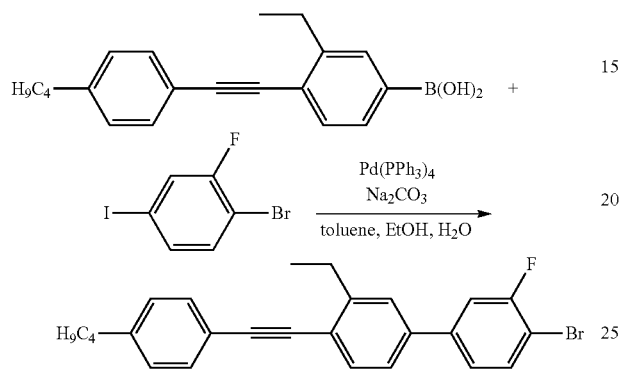

16.8 g (162 mmol) of sodium carbonate and 14.9 g (49 mmol) of 1-bromo-2-fluoro-4-iodobenzene are initially introduced in 60 ml of water and 75 ml of toluene and warmed to 70° C. 1.6 g (1.4 mmol) of tetrakis(triphenylphosphine)-palladium(0) and 15 g (49 mmol) of the boronic acid obtained in the preceding reaction in 50 ml of ethanol are then added dropwise, and the mixture is heated under reflux for 16 h. Work-up is carried out by addition of MTB and water. The phases are separated, and the aqueous phase is extracted twice with MTB. The combined organic phases are washed with saturated sodium chloride solution, dried over sodium sulfate, filtered and evaporated in a rotary evaporator. The residue is purified by column chromatography ($SiO_2$, heptane/toluene=9:1); the further purification is carried out by recrystallisation from isopropanol.

1.4 Synthesis of 3,4,5-trifluoro-2'-fluoro-3"-ethyl-4"-(4-n-butylphenylethynyl)-p-terphenyl (1)

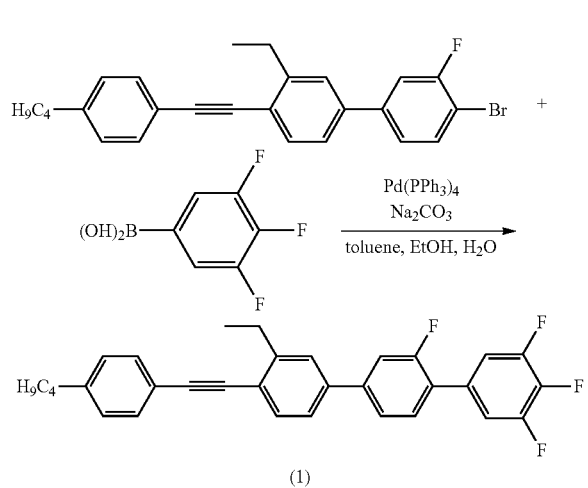

3.3 g (31.1 mmol) of sodium carbonate and 5 g (11.5 mmol) of the bromide obtained in the preceding reaction are initially introduced in 15 ml of water and 60 ml of toluene and warmed to 70° C. 640 mg (0.55 mmol) of tetrakis-(triphenylphosphine)palladium(0) and 2.4 g (13.6 mmol) of 3,4,5-trifluorophenyl-boronic acid in 25 ml of ethanol are then added dropwise, and the mixture is heated under reflux for 16 h. Work-up is carried out by addition of MTB and water, the phases are separated, and the aqueous phase is extracted with MTB. The combined organic phases are washed with saturated sodium chloride solution, dried over sodium sulfate, filtered and evaporated in a rotary evaporator. The residue is purified by column chromatography ($SiO_2$, heptane/toluene=9:1). The further purification is carried out by recrystallisation from ethanol.

MS (EI): m/e (%)=486 (100, M$^+$), 443 (40, [M-propyl]$^+$).
C, 76; N, 159; I.
$\Delta\epsilon$=+16
$\Delta n$=0.35
$\gamma_1$=2.5 Pa·s The following are synthesised analogously or comparably:

2. 3-Fluoro-4-trifluoromethoxy-2'-fluoro-3"-ethyl-4"-(4-n-butylphenylethynyl)-p-terphenyl (2)

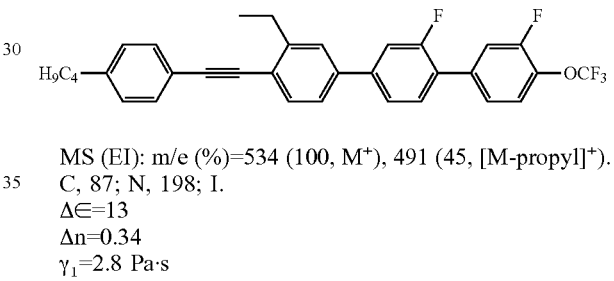

MS (EI): m/e (%)=534 (100, M$^+$), 491 (45, [M-propyl]$^+$).
C, 87; N, 198; I.
$\Delta\epsilon$=13
$\Delta n$=0.34
$\gamma_1$=2.8 Pa·s 3. 3-Fluoro-4-cyano-2'-fluoro-3"-ethyl-4"-(4-n-butylphenylethynyl)-p-terphenyl

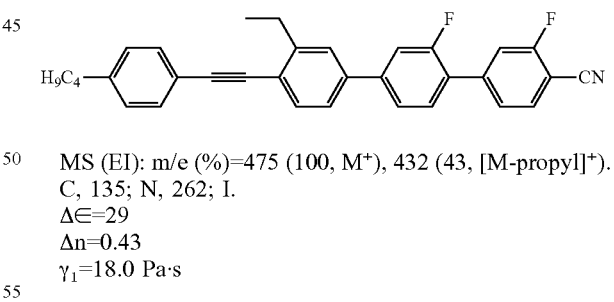

MS (EI): m/e (%)=475 (100, M$^+$), 432 (43, [M-propyl]$^+$).
C, 135; N, 262; I.
$\Delta\epsilon$=29
$\Delta n$=0.43
$\gamma_1$=18.0 Pa·s 4. 3,5-Difluoro-4-trifluoromethoxy-2'-fluoro-3"-ethyl-4"-(4-n-butylphenyl-ethynyl)-p-terphenyl (4)

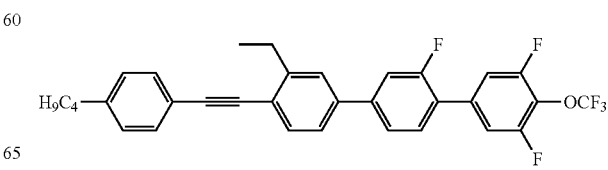

MS (EI): m/e (%)=552 (100, M⁺), 537 (7, [M-methyl]⁺), 509 (45, [M-propyl]⁺).

C, 87; N, 169; I.

Δε=17

Δn=0.33

$\gamma_1$=2.4 Pa·s 5. 3,5-Difluoro-4-trifluoromethyl-2'-fluoro-3''-ethyl-4''-(4-n-butylphenyl-ethynyl)-p-terphenyl

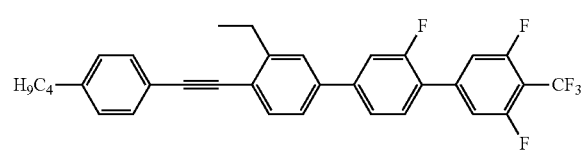

MS (EI): m/e (%)=536 (100, M⁺), 521 (6, [M-methyl]⁺), 493 (50, [M-propyl]⁺).

C, 113; N, 144; I.

Δε=22

Δn=0.34

$\gamma_1$=3.4 Pa·s 6. 3,4,5-Trifluoro-2'-fluoro-3''-ethyl-4''-(4-n-hexylphenylethynyl)-p-terphenyl

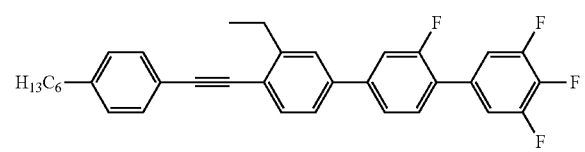

MS (EI): m/e (%)=514 (100, M⁺), 499 (6, [M-methyl]⁺), 443 (44, [M-pentyl]⁺).

C, 77; N, 144; I.

Δε=13

Δn=0.34

$\gamma_1$=2.7 Pa·s 7. 3,4,5-Trifluoro-3''-ethyl-4''-(4-n-butylphenylethynyl)-p-terphenyl

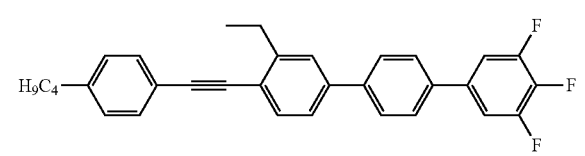

MS (EI): m/e (%)=468 (100, M⁺), 453 (8, [M-methyl]⁺), 425 (39, [M-propyl]⁺), 410 (21, [M-methyl-propyl]⁺).

C, 75; N, 184; I.

Δε=12

Δn=0.37

$\gamma_1$=2.2 Pa·s 8. 3,4-Difluoro-3''-ethyl-4''-(4-n-butylphenylethynyl)-p-terphenyl

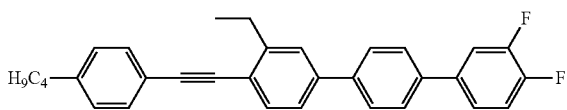

MS (EI): m/e (%)=450 (100, M⁺), 435 (8, [M-methyl]⁺), 407 (35, [M-propyl]⁺), 392 (22, [M-methyl-propyl]⁺).

C, 106; N, 231; I.

Δε=7

Δn=0.40

$\gamma_1$=3.9 Pa·s 9. 3,4,5-Trifluoro-2'-fluoro-2''-fluoro-3''-propyl-4''-(4-n-butylphenylethynyl)-p-terphenyl

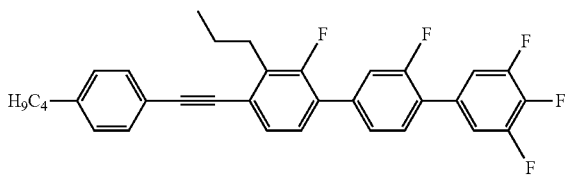

MS (EI): m/e (%)=518 (100, M⁺), 503 (5, [M-methyl]⁺), 489 (26, [M-ethyl]⁺), 475 (16, [M-propyl]⁺), 461 (10, 446 (27).

Tg −31 C, 95; N, 105; I.

Δε=24

Δn=0.30

$\gamma_1$=2.7 Pa·s 10. 4-(3,4,5-Trifluorophenylethynyl)-3-ethyl-2'-fluoro-4''-n-butyl-p-terphenyl

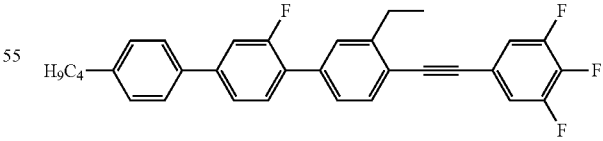

MS (EI): m/e (%)=486 (100, M⁺), 443 (66, [M-propyl]⁺), 428 (12, [M-methyl-propyl]⁺).

C, 89; N, 160; I.

Δε=18

Δn=0.35

$\gamma_1$=1.3 Pa·s

11. 4-(3,4,5-Trifluorophenylethynyl)-3-ethyl-2'-fluoro-4'-n-butyl-p-biphenyl

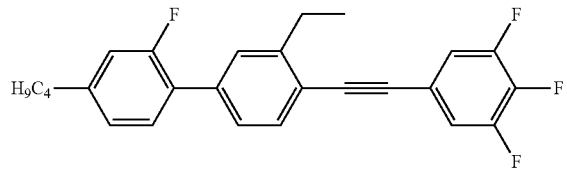

MS (EI): m/e (%)=410 (100, M⁺), 395 (6, [M-methyl]⁺), 367 (74, [M-propyl]⁺), 352 (17, [M-methyl-propyl]⁺).
Tg −51 C, 25; I.
$\Delta\epsilon=10$
$\Delta n=0.22$
$\gamma_1=0.2$ Pa·s

12. 4-(3,4,5-Trifluorophenylethynyl)-2-ethyl-2',6'-difluoro-4'-n-butyl-p-biphenyl

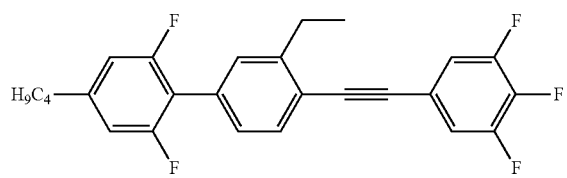

MS (EI): m/e (%)=428 (100, M⁺), 413 (20, [M-methyl]⁺), 385 (39, [M-propyl]⁺), 370 (20, [M-methyl-propyl]⁺).
C, 59; I.
$\Delta\epsilon=14$
$\Delta n=0.20$
$\gamma_1=0.2$ Pa·s

13. 3,4,5-Trifluoro-3',4'-(n-butylphenylethynyl)-p-biphenyl

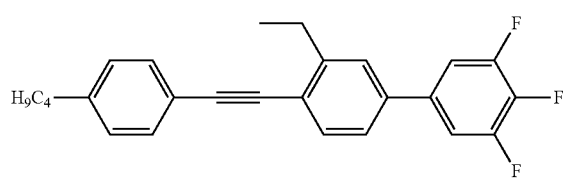

MS (EI): m/e (%)=392 (100, M⁺), 377 (10, [M-methyl]⁺), 349 (84, [M-propyl]⁺), 334 (36, [M-methyl-propyl]⁺).
Tg −47 I
$\Delta\epsilon=9$
$\Delta n=0.25$
$\gamma_1=0.3$ Pa·s

Mixture Example 1

A liquid-crystal medium M-1 having the composition and properties as indicated in the following table is prepared. Compound (1) (No. 15) originates from Synthesis Example 1.

| Composition Compound | | |
|---|---|---|
| No. | Abbreviation | |
| 1 | BCH-3F.F | 10.8% |
| 2 | BCH-5F.F | 9.0% |
| 3 | ECCP-30CF3 | 4.5% |
| 4 | ECCP-50CF3 | 4.5% |
| 5 | CBC-33F | 1.8% |
| 6 | CBC-53F | 1.8% |
| 7 | CBC-55F | 1.8% |
| 8 | PCH-6F | 7.2% |
| 9 | PCH-7F | 5.4% |
| 10 | CCP-20CF3 | 7.2% |
| 11 | CCP-30CF3 | 10.8% |
| 12 | CCP-40CF3 | 6.3% |
| 13 | CCP-50CF3 | 9.9% |
| 14 | PCH-5F | 9.0% |
| 15 | (1) | 10.0% |
| Σ | | 100.0% |

| Physical properties | |
|---|---|
| T(N, I) = | 96° C. |
| Δn (20° C., 589.3 nm) = | 0.124 |
| Δε (20° C., 1 kHz) = | 4.9 |
| $\gamma_1$ (20° C.) = | 166 mPa·s |

This mixture is used for applications in the microwave region, in particular for phase shifters for phased-array antennae.

For comparison, a medium C-1 without component (1) is prepared from compound Nos. 1-14 of medium M-1, where compound Nos. 1-14 are present in the same relative amounts.

Mixture Examples 2 and 3

Liquid-crystal media M-2 and M-3 having the composition of M-1 are prepared with the difference that for M-2, compound (2) from Synthesis Example 2 is employed instead of compound (1), and for M-3, compound (4) from Synthesis Example 4 is employed instead of compound (1).

The results for the mixture examples are shown in the following table.

TABLE

Properties of mixtures M-1, M-2, M-3 and C-1 (comparison) at 19 GHz (20° C.)

| Mixture | $\epsilon_{r,\parallel}$ | $\epsilon_{r,\perp}$ | τ | tan $\delta_{\epsilon,r,\parallel}$ | tan $\delta_{\epsilon,r,\perp}$ | η |
|---|---|---|---|---|---|---|
| M-1 | 2.63 | 2.29 | 0.130 | 0.0045 | 0.0116 | 11.2 |
| M-2 | 2.64 | 2.31 | 0.127 | 0.0047 | 0.0129 | 9.82 |
| M-3 | 2.62 | 2.30 | 0.125 | 0.0046 | 0.0119 | 10.46 |
| C-1 | 2.56 | 2.29 | 0.107 | 0.0049 | 0.0126 | 8.50 |

The tuneability τ and the material quality η are significantly improved for mixtures M-1, M-2 and M-3 compared with comparative mixture C-1.

The invention claimed is:
1. A compound of formula I

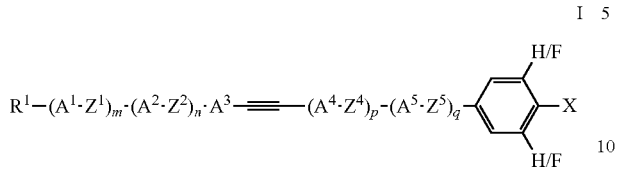

in which
H/F means H or F,
$A^{1-5}$ independently of one another, denote
  a) 1,4-phenylene, in which one or more CH groups are optionally replaced by N, or
  b) a radical of one of the following formulae

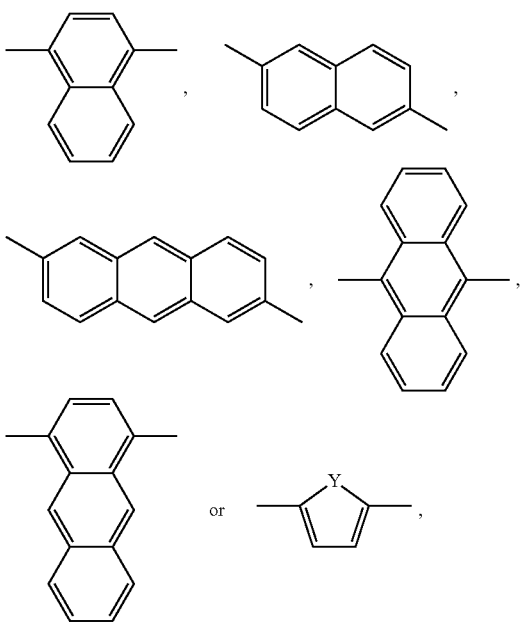

wherein in a) and b), optionally one or more H atoms are independently replaced by L, which L in a) and b) each, independently of one another, denotes Br, Cl, F, CN, —NCS, —SCN, $SF_5$, $C_1$-$C_{10}$ alkyl, $C_1$-$C_{10}$ alkoxy, $C_3$-$C_6$ cycloalkyl or a mono- or polyfluorinated $C_1$-$C_{10}$ alkyl or alkoxy group,
and wherein one of the rings $A^3$ and $A^4$ denotes

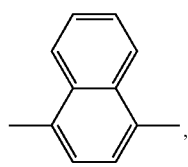

Y denotes S or O,
$R^1$ denotes a halogenated or unsubstituted alkyl radical having 1 to 15 C atoms, in which one or more $CH_2$ groups are optionally replaced, independently of one another, by —CH=CH—, —CF=CF—, —CF=CH—, —CH=CF—, —(CO)O—, —O(CO)—, —(CO)—, —O— or —S— in such a way that O or S atoms are not linked directly to one another, or denotes F, Cl, Br, CN, SCN, NCS or $SF_5$,
X denotes F, Cl, Br, CN, SCN, NCS, $SF_5$ or a halogenated alkyl radical having 1 to 15 C atoms, in which one or more $CH_2$ groups are optionally replaced, independently of one another, by —CH=CH—, —CF=CF—, —CF=CH—, —CH=CF—, —(CO)O—, —O(CO)—, —(CO)—, —O— or —S— in such a way that O or S atoms are not linked directly to one another,
$Z^1$, $Z^2$, $Z^4$, $Z^5$ all denote a single bond, and
m, n, p, q independently denote 0 or 1, where m+n+p+q is 1, 2, 3 or 4.

2. A compound according to claim 1, wherein $A^3$ denotes 1,4-phenylene, in which one or more CH groups are optionally replaced by N.

3. A compound according to claim 1, wherein m and n are 0.

4. A compound according to claim 1, wherein $A^1$, $A^2$, $A^5$ and one of $A^3$ or $A^4$, if present, each denote an optionally substituted 1,4-phenylene ring.

5. A compound according to claim 1, wherein m+n+p+q is 1.

6. A liquid-crystal medium, comprising one or more compounds according to claim 1.

7. A liquid-crystal medium according to claim 6, further comprising one or more compounds of formula II:

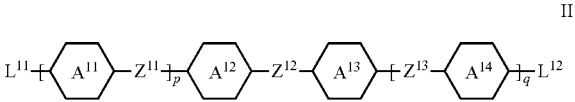

in which:
$L^{11}$ denotes $R^{11}$ or $X^{11}$,
$L^{12}$ denotes $R^{12}$ or $X^{12}$,
$R^{11}$ and $R^{12}$ independently of one another, denote unfluorinated alkyl or unfluorinated alkoxy having 1 to 17 C atoms, or unfluorinated alkenyl, unfluorinated alkynyl, unfluorinated alkenyloxy or unfluorinated alkoxyalkyl having 2 to 15 C atoms,
$X^{11}$ and $X^{12}$ independently of one another, denote F, Cl, Br, CN, NCS, SCN, $SF_5$, or fluorinated alkyl or fluorinated alkoxy having 1 to 7 C atoms, or fluorinated alkenyl, fluorinated alkenyloxy or fluorinated alkoxyalkyl having 2 to 7 C atoms,
p, q independently denote 0 or 1,
$Z^{11}$ to $Z^{13}$ independently of one another, denote trans-CH=CH—, trans-CF=CF—, —C≡C— or a single bond, and

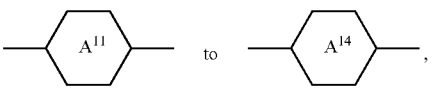

independently of one another, denote

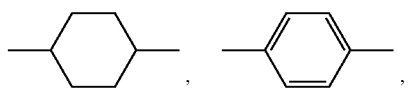

-continued

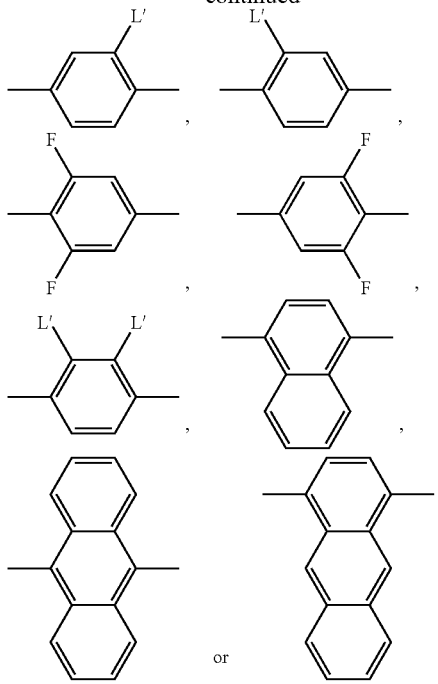

L' independently denotes branched or unbranched alkyl, alkenyl or alkynyl having 1 to 12 C atoms, in which, independently of one another, one or more CH$_2$ groups are optionally replaced by O, or denotes C$_3$-C$_6$ cycloalkyl, C$_3$-C$_6$ cycloalkenyl, fluorinated alkyl or alkenyl, fluorinated alkoxy or alkenyloxy, F, Cl, Br, CN, NCS, SCN or SF$_5$.

8. A liquid-crystal medium according to claim 6, wherein the concentration of the compounds of formula I in total is 5% to 95%.

9. A process for preparing a liquid-crystal medium according to claim 6, comprising mixing together one or more compounds of formula I with one or more further compounds and optionally with one or more additives.

10. A component for high-frequency technology, which contains a liquid-crystal medium according to claim 6.

11. A component according to claim 10, which comprises one or more functionally connected phase shifters.

12. A phased array antenna, which comprises one or more components according to claim 10.

13. A compound according to claim 1, wherein L each, independently of one another, denotes methyl, ethyl or straight or branched propyl.

14. A compound according to claim 1, wherein L each, independently of one another, denotes cyclopropyl.

15. A compound according to claim 1, wherein one of the rings A$^3$ and A$^4$ denotes

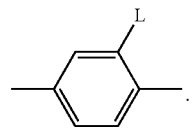

16. A compound according to claim 1, wherein one of the rings A$^3$ and A$^4$ denotes

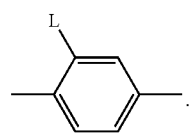

17. A compound according to claim 1, wherein one of the rings A$^3$ and A$^4$ denotes

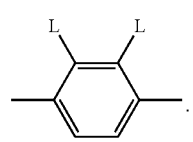

18. A compound according to claim 1, wherein
R$^1$ denotes an unsubstituted alkyl radical having 1 to 15 C atoms, in which one or more CH$_2$ groups are optionally replaced, independently of one another, by —CH═CH—, —CF═CF—, —CF═CH—, —CH═CF—, —(CO)O—, —O(CO)—, —(CO)—, —O— or —S— in such a way that O or S atoms are not linked directly to one another, or denotes F, Cl, Br, CN, SCN, NCS or SF$_5$.

19. A compound according to claim 1, wherein
X denotes F, Cl, Br, SCN, NCS, SF$_5$ or a halogenated alkyl radical having 1 to 15 C atoms, in which one or more CH$_2$ groups are optionally replaced, independently of one another, by —CC—, —CH═CH—, —CF═CF—, —CF═CH—, —CH═CF—, —(CO)O—, —O(CO)—, —(CO)—, —O— or —S— in such a way that O or S atoms are not linked directly to one another.

20. A compound according to claim 1, wherein m+n is 0 or 1.

* * * * *